United States Patent [19]

Gaffar et al.

[11] Patent Number: 4,759,925

[45] Date of Patent: Jul. 26, 1988

[54] ANTIPLAQUE ORAL COMPOSITION CONTAINING PERFLUOROALKYL SULFATE SURFACTANT

[75] Inventors: Abdul Gaffar, Princeton; Anthony Esposito, Roselle, both of N.J.

[73] Assignee: Colgate-Palmolive Company, New York, N.Y.

[21] Appl. No.: 106,097

[22] Filed: Oct. 8, 1987

[51] Int. Cl.$^4$ ................................................ A61K 7/18
[52] U.S. Cl. ...................................... 424/52; 514/901; 424/57
[58] Field of Search ...................... 424/52, 57; 514/901

[56] References Cited

U.S. PATENT DOCUMENTS 2,829,086 4/1958 Kirschenbauer ...................... 424/52

OTHER PUBLICATIONS

*Chemical Abstracts*, vol. 90, No. 2, Jan. 8, 1979, p. 117, Abst. No. 123623w, "Method and Composition for Removing Calcium Sulfate Scale Deposits from Surfaces".

Gaffar, *J. of Pharmaceutical Science*, vol. 74, No. 11, Nov. 1985.

*Primary Examiner*—J. R. Brown
*Assistant Examiner*—F. T. Moezie
*Attorney, Agent, or Firm*—Robert L. Stone; Murray M. Grill

[57] ABSTRACT

The perfluoroalkyl surfactant (PAS) of the general formula $C_xF_{2x+1}(CH_2)_nS(CH_2)_{n'}CO_2M$ wherein x is an integer of 3–8, each of n and n' is an interger of 2–4 and may be the same or different and M is hydrogen, an alkali metal or ammonium, provides an oral composition, such as a dentifrice or a mouthwash with effect in prevent plaque formation. A preferred PAS is Zonyl FSA, $C_{3-8}F_{7-17}(CH_2)_2S(CH_2)_2COOLi$.

9 Claims, No Drawings

ANTIPLAQUE ORAL COMPOSITION CONTAINING PERFLUOROALKYL SULFATE SURFACTANT

BACKGROUND AND PRIOR ART

This invention relates to an oral composition which is effective in preventing formation of dental plaque. Dental plaque results when cariogenic bacteria aggregate in colonies and form a tenacious deposit on dental or tooth surfaces. The presence of plaque on teeth is unsightly and may be a precursor to development of gingivitis, dental caries and periodontal disease.

Many attempts have been made to control the effects of cariogenic bacteria and the dental plaque they produce, for example, fluoride application, flossing, brushing, etc. Such treatments are typically directed to either counteracting the secondary effects of plaque on the teeth and gums or to removing plaque that is already formed on and adhering to the teeth and surrounding tissue.

It is generally recommended that such "home treatments" to reduce plaque to supplemented with periodic professional treatment by a dentist. Proposals which might reduce the need for professional antiplaque treatment have been directed to forming a barrier, membrane or film on dental surfaces to thereby prevent bacteria from reaching the dental surfaces. Compounds and compositions for barrier, membrane or film formation are described in a series of patents of R. W. H. Chang of Minnesota Mining and Manufacturing Company (3M); particularly U.S. Pat. Nos. 4,510,127; 4,485,090; 4,470,964; 4,428,930; 4,436,146; 4,304,766 (reissued as RE. 31,787); and 4,243,658. Barrier formations are also described in U.S. Pat. Nos. 4,360,512 of J. D. Vidra of Johnson & Johnson Products Inc. and 4,216,200 of W. E. Horn.

However, proposals for barrier or film formation do not necessarily avoid the need for treatment by a dentist and also have physiologic disadvantage that they introduce an artificial material into the oral environment which is permanent or at least long-lasting and which could alter the total ecologic balance within the oral cavity.

Accordingly, the present invention is directed to preventing formation of bacterial plaque on dental surfaces to a very substantial degree without introducing an artificial barrier or film.

In the patents to 3M mentiond above, polymeric and nonpolymeric forming a barrier, membrance on teeth, not only prevent plaque from forming but also prevent other previously applied water-soluble hygenic or therapeutic materials, such as anticaries fluoride compounds from eluting from the teeth to thereby provide prolonged activity. In U.S. Pat. No. 2,829,086 to H. G. Kirschenbauer of Colgate-Palmolive Company, coating compounds which are perfluoro monocarboxylic acid compounds of the formula $C_nF_{2+1}COOX$, wherein n is an integer of at least 5 and X is hydrogen or a water-soluble salt form cation, are also disclosed as antibacterial compounds for oral use.

In the patents to 3M, the barrier materials include nonpolymeric anionic membrane-forming materials which are perfluoroalkyl surfactants (hereinafter "PAS") such as compounds having the general formula:

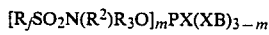

wherein $R_f$ is a monovalent, stable, inert, fluorinated, saturated aliphatic nonpolar radical; $R^2$ is hydrogen, alkyl of from 1 to 6 carbon atoms, aryl, cycloalkyl, aralkyl or alkaryl; $R^3$ is an alkylene, arylene, alkarylene or aralkylene bridging group containing from 1 to 12 carbon atoms, m is 1 or 2; X is oxygen or sulfur; and B is hydrogen, alkyl, aryl, cycloalkyl, alkaryl, or aralkyl (each of up to 20 carbon atoms), alkali metals (e.g., sodium, potassium lithium, etc.), ammonium, or amine groups.

A preferred compound of the foregoing general formula is indicated to be $C_8F_{17}SO_2N(C_2H_5)CH_2CH_2OPO_2H_2$, (perfluorosulfonamidoalkyl ester of phosphorous acid, hereinafter "PSEAP").

Another type of PAS disclosed in the 3M patents has the formula:

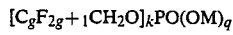

wherein M is selected from hydrogen, alkali metal (e.g., sodium, potassium, lithium), ammonium and amine groups, and g is an integer of from 1 to 10, k is 1 or 2 and q is 3−k. It is stated that such materials are available from E. I. duPont de Nemours as "Zonyl FSP".

The materials of the 3M patents are stated to effect their antiplaque effect by forming a barrier membrane on dental surfaces. It is the observation of the present inventors that materials of the general formulae in the 3M patents, such as PSEAP, do indeed provide antiplaque effect as a result of the artificial barrier formation. However, the Zonyl FSP material of DuPont, actually has the formula:

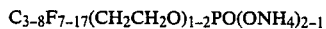

which is not included within the general formula set forth in the 3M patents. Moreover, its antiplaque effectiveness is moderate and does not appear to be substantially attributable to artificial barrier formation.

It is an advantage of the present invention that a PAS material is provided which has a high degree of antiplaque effectiveness and does not cause permanent or long-lasting retentive formation of an artificial barrier layer on dental surfaces. Any layer which may form is at most transient.

Other advantages will be apparent from consideration of the following description.

In accordance with certain of its aspects, this invention relates to an oral composition comprising a vehicle comprising water and humectant and containing therein an effective antiplaque amount of a perfluoroalkyl surfactant (PAS) of the general formula:

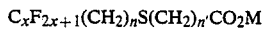

wherein x is an integer of 3-8, each of n and n' is an integer of 2-4 and may be the same or different and M is hydrogen, an alkali metal or ammonium. PAS of the general formula:

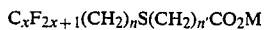

wherein x is an integer of 3-8, each of n and n' is an integer of 2-4 and may be the same or different and M is hydrogen, an alkali metal or ammonium is employed in oral compositions in amount effective in preventing plaque format on, typically at least about 0.05%, for instance about 0.05–10%, preferably about 0.1–2% by weight in a mouthrinse and about 0.5–5% in a dentifrice.

The PAS which is preferred is commercially available from DuPont as Zonyl FSA. Zonyl FSA is particularly characted with each of "n" and "n'" being 2 and the cation "M" being Li. Its properties, when neutralized to pH 7-8 with sodium hydroxide include:

| Zonyl FSA Physical Properties | |
| --- | --- |
| Ionic Type | Anionic |
| Physical Form | Liquid |
| Percent Solids | 50 |
| Diluent | Water/Isopropyl Alcohol, 25:25 |
| Density 25° C.(77° F.) | |
| g/mL (Mg/m$^3$) | 1.17 |
| lb/gal | 9.7 |
| Flash Point, Pensky Martins Closed Tester | |
| °C. | 21 |
| °F. | 69 |
| Aqueous Surface Tensions dynes/cm (mN/m), 25° C.(77° F.) | |
| 0.01% Solids | 22 |
| 0.10% Solids | 18 |
| Color | Dark Amber |
| Melting Point | |
| °C. | −18 |
| °F. | 0 |
| Vapor Pressure | |
| p/si @ 100° F. | <16 |
| k/pa 37.8° C. | <110.32 |
| Zonyl FSA Chemical Properties | |
| Stability, 25° C.(77° F.) ("S" = Stable, "I" = Insoluble) | |
| 25% Sulfuric Acid | 1 |
| 37% Hydrochloric Acid | 1 |
| 70% Nitric Acid | 1 |
| 10% Potassium Hydroxide | S |
| Solubility, 25° C.(77° F.) g Solids/100 g Solution | |
| Water | >2 |
| Isopropyl Alcohol | 0.1 |
| 1:1 Water/Isopropyl Alcohol | >2 |
| Methyl Alcohol | >2 |
| Acetone | 0 |
| Ethyl Acetate | 0 |
| Toluene | 0 |
| n-Heptane | 0 |
| Tetrahydrofuran | 0 |
| Methyl Chloroform | 0 |
| Hydrochloric acid | insoluble |
| Ethanol | soluble |
| sodium hydroxide | soluble |

It is noteworthy that while the anti-plaque PAS material contains a substantial amount of fluoride it does not provide substantial anticaries effect. Should it be desired to provide anticaries effect in an oral composition containing the PAS material, it is desirable to include in the oral composition a water-soluble fluoride-providing compound such as sodium fluoride, stannous fluoride, potassium fluoride, ammonium fluoride, stannous chlorofluoride, hexylamine hydrofluoride, myristylamine hydrofluoride, betaine fluoride, glycine potassium fluoride, cuprous fluoride, zinc fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal fluoride-providing compounds, such as sodium fluoride, sodium monofluorophosphate (MFP) and mixtures thereof, are preferred.

The amount of the fluoride-providing compound is dependent to some extent upon the type of compound, its solubility, and the type of oral preparation, but it is a nontoxic amount. An amount of such compound which releases a maximum of about 1% of fluoride ion by weight of the preparation is substantially rheologically satisfactory. Any suitable minimum amount of such compound may be used, but it preferable to employ sufficient compound to release about 0.005 to 1%, and preferably about 0.1% of fluoride ion. Typically, in the case of sodium monofluorophosphate, this compound is present in an amount of about 0.01 to about 7.6% by weight, based on the weight of the preparation, and preferably in the range of about 0.05 to about 1% by weight, especially about 0.76%.

When the fluoride-providing compound is present, it is desirable that the weight ratio of PAS to fluoride-providing compound is about 0.5:1 to about 2:1.

When the oral composition is a dentifrice it contains a polishing material, generally water-insoluble and in amount of about 15–75%, preferably about 15–30% when the polishing material is siliceous in nature and about 25–50% or more when it is not. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, alumina, hydrated alumina, aluminum silicate, zirconium silicate, silica, including silica containing combined alumina, e.g. sodium aluminosilicate, bentonite, and mixtures thereof. Preferred polishing materials include siliceous material such as complex amorphous sodium aluminosilicate, as well as hydrated alumina, calcium carbonate and dicalcium phosphate. The polishing materials may be used in admixture. In a dentifrice liquid and solid vehicle materials should necessarily be proportioned to form a creamy or gel mass of desired consistency which is extrudable from a collapsible lined or unlined aluminum tube, lined lead tube, laminate tube, mechanically operated dispenser or pressure operated dispenser. In general, the liquids in the dentifrice will comprise chiefly water and humectant, such as glycerine, sorbitol, propylene glycol, polyethylene glycol, etc., including suitable humectant mixtures. It is advantageous usually to use a mixture of both water and a humectant such as glycerine or sorbitol. The total liquid content will generally be about 20–75% by weight of the formulation. The amount of water is typically about 3–30% by weight and the amount of humectant is typically about 20–72% by weight. It is preferred to use a gelling agent in the dentifrice, the natural and synthetic gums and gum-like materials, e.g., Irish moss, gum tragacanth, sodium carboxymethyl cellulose, polyvinyl pyrrolidone, starch, and the like usually, in an amount up to about 10% by weight, and preferably about 0.5–5% of the formulation.

In an aqueous mouthrinse, non-toxic alcohol (e.g. ethanol or iso-propanol) is typically present in amount of about 5–25% by weight. Water typically comprises at least 50% by weight of a mouthrinse and humectant about 5–40% by weight.

The alcohol component of a mouthwash is a nontoxic alcohol such as isopropanol or ethanol, preferably utilizing denaturating components which also function as flavoring agents. These flavoring agents are used in an amount between about 1% and 2% of the total alcohol content of the mouthwash.

Various adjuvant materials can be incorporated in the oral compositions. Added materials in the formulation which do not substantially adversely effect the properties and characteristics can be suitably selected and used in proper amount depending upon the particular type of preparation. Such materials which may be used include soluble saccharin, flavoring oils (e.g., menthol and oils of spearmint, peppermint, wintergreen), coloring or whitening agents (e.g. titanium dioxide), preservatives (e.g. sodium benzoate, etc.), and the like. Various other materials can be added such as additional surfactant or surface-active agent, e.g. sodium lauryl sulfate and $C_{10}$–$C_{18}$ fatty acid amides of amino carboxylic acid compounds, typically sodium lauroyl and palmitoyl sarcosides. Nonionic surface active agents such as block copolymers of polyoxyethylene and polyoxypropylene can be employed. Other suitable materials are chlorophyllin and various ammoniated ingredients, such as urea, diammonium phosphate and mixtures thereof.

The present invention is further illustrated in the following examples, wherein amounts are by weight unless otherwise indicated.

EXAMPLE 1

The effects of PAS materials on cell adsorbing attachmemt of plaque forming bacteria on teeth is determined in accordance with the in vitro procedure described in J. Pharmaceutical Sciences, Vol. 74, No. 11, Pages 1228–1232, 1985, by A. Gaffar, et al.

Saliva coated hydroxyapatite disks (SHA) are treated with the respective surfactants for 5 min., washed with buffered and the adsorption of A. viscosus is determined with the following results:

| Treatment of SHS | % Cell Adsorbed | % Relative to Control |
|---|---|---|
| Control disk treated with phosphate buffer | 38.1% | 100 |
| Control disk treated with solvent (0.5% propanol) | 29.3% | 76.9% |
| 0.1% I Surfactant | 13.6% | 35.7% |
| 0.1% II Surfactant | 16.5% | 43.3% |

I. Surfactant Zonyl FSA ex DuPont
$C_{3-8}F_{7-17}(CH_2)_2S(CH_2)CO_2Li$
II. surfactant Zonyl FSP ex DuPont
$C_{3-8}F_{7-17}(CH_2CH_2O)_{1-2}PO(ONH_4)$ The data showed that compared to two controls, the coated disks treated with both PAS surfactants inhibited the adsorption of the organisms to SHA.

EXAMPLE 2

The effects of PAS materials on formations in rats is determined in accordance with the procedure described in the aforementioned article by A. Gaffar, et al in J. Pharmaceutical Sciences, with the following results:

| Treatment | N | PE + SEM | % Reduction Sig. | Mean Dental Caries + SEM Smooth Surface | Fissures |
|---|---|---|---|---|---|
| Placebo | 12 | 2.5 ± 0.18 | — | 13.2 ± 1.11 | 5.6 ± 0.77 |
| 1% Solution of I | 12 | 1.6 ± 0.18 | −36% (P < 0.001) | 14.3 ± 1.11 | 7.6 ± 0.77 |
| 1% Solution of II | 12 | 2.1 ± 0.18 | −16% (non-Sig.) | 13.8 ± 1.11 | 7.3 ± 0.77 |
| 0.5% Chlorhexidine | 12 | 1.2 ± 0.18 | −52% | 4.2 ± 1.11 | 3.5 ± 0.77 |

I is Zonyl FSA
II is Zonyl FSP
N is number of rates
PE is Plaque Extent
SEM is Standard error of mean
P is probability (less than or equal to 0.001.0 is significant to 99.999%)

The results show that compared to the placebo, perfluoroanionic Surfactant (I) Zonyl FSA, signicantly (P<0.001) reduces plaque. It does not reduce caries. By comparison, perfluoroanionic Surfactant (II), Zonyl FSP does not reduce caries and does not significantly reduce plaque. The positive control, 0.5% chlorhexidine, reduces both plaque and caries. It is thus seen that perfluoroalkyl carboxylate (I) is effective against plaque in vivo.

EXAMPLE 3

| Mouthrinse Composition | |
|---|---|
| | % |
| Ethanol | 10 |
| Glycerine | 10 |
| Flavor | 0.146 |
| Polyoxyethylene - Polyoxypropylene (Pluronic F108) | 3.0 |
| PAS (I) | 1.0 |
| Saccharin | 0.03 |
| Water | Q.S. to 100 |

PAS (I) is Zonyl FSA

EXAMPLE 4

| Dentifrice Composition | |
|---|---|
| | % |
| PAS (I—Na) | 3.0 |
| Sodium fluoride | 0.22 |
| Sodium Benzoate | 0.50 |
| Sodium Saccharin | 0.20 |
| Sodium Carboxymethyl Cellulose | 1.40 |
| Glycerine | 25.0 |
| Silica Containing Combined Alumina | 30.0 |
| Sodium lauryl sulfate | 1.50 |
| Flavor | 1.00 |
| Water | Q.S. to 100 |

PAS (I—Na) is Zonyl FSA modified as the sodium salt

Although this invention has been described with regard to specific example; it will be apparent to one skilled in the art that various modifications may be made thereto which fall within its scope.

We claim:
1. An oral composition comprising a vehicle comprising water and humectant and containing therein an effective antiplaque amount of a perfluoroalkyl surfactant (PAS) of the general formula:

$$C_xF_{2x+1}(CH_2)_nS(CH_2)_{n'}CO_2M$$

wherein x is an integer of 3-8, each of n and n' is an integer of 2-4 and may be the same or different and M is hydrogen, an alkali metal or ammonium.

2. The oral composition claimed in claim 1 wherein said surfactant has the general formula:

$$C_xF_{2x+1}(CH_2)_2S(CH_2)_2COOLi.$$

3. The oral composition claimed in claim 1 wherein water is present in amount of about 3-30% and humectant is present in amount of about 20-72% by weight, said oral composition comprises about 0.5-10% by weight of a gelling agent and about 15-75% by weight of dentally acceptable water-insoluble polishing agent and said oral composition is a dentifrice.

4. The oral composition claimed in claim 1 wherein water is present in amount of at least about 50% by weight, humectant is present in amount of about 5-40% by weight and said oral composition comprises about 5-25% of a non-toxic alcohol and is a mouthrinse.

5. The oral composition claimed in claim 1 wherein said surfactant is present in amount of at least about 0.05% by weight.

6. The oral composition claimed in claim 3 wherein said surfactant is present in amount of about 0.5-5% by weight.

7. The oral composition claimed in claim 4 wherein said surfactant is present in amount of about 0.1-2% by weight.

8. The oral composition claimed in claim 1 wherein a water-soluble fluoride-providing material is present in amount sufficient to release about 0.005-1% by weight of fluoride.

9. The oral composition claimed in claim 8 wherein said water-soluble fluoride-providing compound is selected from the group consisting of sodium fluoride, sodium monofluorophosphate and mixtures thereof.

* * * * *